United States Patent
Wu et al.

(10) Patent No.: US 11,427,532 B2
(45) Date of Patent: Aug. 30, 2022

(54) FLUORESCENT COMPOUND FOR DETECTION OF ISOCYANATE SUBSTANCES, PREPARATION METHOD AND USE THEREOF AS TEST-PAPER-TYPE DETECTION PROBE

(71) Applicant: SOUTH CHINA UNIVERSITY OF TECHNOLOGY, Guangdong (CN)

(72) Inventors: Shuizhu Wu, Guangdong (CN); Lingfeng Xu, Guangdong (CN); Fang Zeng, Guangdong (CN)

(73) Assignee: SOUTH CHINA UNIVERSITY OF TECHNOLOGY, Guangzhou (CN)

( * ) Notice: Subject to any disclaimer, the term of this patent is extended or adjusted under 35 U.S.C. 154(b) by 0 days.

(21) Appl. No.: 17/298,951

(22) PCT Filed: Oct. 28, 2019

(86) PCT No.: PCT/CN2019/113788
§ 371 (c)(1),
(2) Date: Jun. 2, 2021

(87) PCT Pub. No.: WO2021/000467
PCT Pub. Date: Jan. 7, 2021

(65) Prior Publication Data
US 2022/0041545 A1    Feb. 10, 2022

(30) Foreign Application Priority Data

Jun. 29, 2019    (CN) .......................... 201910581460.0

(51) Int. Cl.
*G01N 21/78*    (2006.01)
*G01N 21/64*    (2006.01)
(Continued)

(52) U.S. Cl.
CPC ............ *C07C 251/24* (2013.01); *C09K 11/06* (2013.01); *G01N 21/643* (2013.01); *G01N 21/78* (2013.01);
(Continued)

(58) Field of Classification Search
CPC .... G01N 21/643; G01N 21/78; C07C 251/24; C09K 11/06
See application file for complete search history.

(56) References Cited

U.S. PATENT DOCUMENTS 6,656,737 B1    12/2003    Streicher

FOREIGN PATENT DOCUMENTS

CN    108976160    12/2018

OTHER PUBLICATIONS

Weh S. Wu et al., "Application of Tryptamine as a Derivatizing Agent for Airborne Isocyanate Determination—Part 4. Evaluation of Major High-performance Liquid Chromatographic Methods Regarding Airborne Isocyanate Determination With Specific Investigation of the Competitive Rate of Derivatization", Analyst, Jan. 1991, pp. 21-25.

(Continued)

*Primary Examiner* — Brian R Gordon
*Assistant Examiner* — Dwan A Gerido
(74) *Attorney, Agent, or Firm* — JCIPRNET

(57) ABSTRACT

Disclosed is a fluorescent compound for the detection of isocyanate substances, a preparation method therefor and use thereof as a test-paper-type detection probe. The fluorescent compound is 2,4-di(((4'-(diphenylamino)-[1,1'-biphenyl]-4-yl)imino)methyl)phenol. The fluorescent compound is prepared by means of a one-step method. The fluorescent compound has simple and convenient preparation with high yield, and is capable of making a rapid and specific response to isocyanate substances. Moreover, the (Continued)

fluorescence intensity of the fluorescent compound will enhance with the increase of the isocyanate concentration. The fluorescent compound can be made into a portable test-paper-type probe for the detection of isocyanate substances in air, and can achieve the visual detection of volatile isocyanate gases. The probe has an aggregation-induced emission effect, and thus it has higher fluorescence quantum yield when using a test-paper-type probe for detection.

8 Claims, 4 Drawing Sheets

(51) Int. Cl.
  *C07C 251/24* (2006.01)
  *C09K 11/06* (2006.01)
(52) U.S. Cl.
  CPC ............ *C09K 2211/1007* (2013.01); *C09K 2211/1014* (2013.01)

(56) References Cited

OTHER PUBLICATIONS

M. Dalene et al., "Trace Analysis of Airborne Aromatic Isocyanates and Related Aminoisocyanates and Diamines Using High-Performance Liquid Chromatography with Ultraviolet and Electrochemical Detection", Journal of Chromatography, 1988, pp. 469-481.

Laurie H. Kormos et al., "Determination of Isocyanates in Air by Liquid Chromatography with Fluorescence Detection", American Chemical Society, Jun. 1981, pp. 1122-1125.

G. Skarping et al., "Trace Analysis of Isocyanates in Industrial Atmospheres Using Gas Chromatography and Electron-Capture Detection", Journal of Chromatography, 1981, pp. 313-321.

Walter E. Rudzinski et al., "Determination of Hexamethylene Diisocyanate in Spray-Painting Operations Using Capillary Zone Electrophoresis", Anal. Chem., May 1994, pp. 1664-1666.

G. Skarping et al., "Capillary Gas Chromatographic Method for the Determination of Complex Mixture of Isocyanates and Amines", Journal of Chromatography, 1985, pp. 191-204.

Kalman Marcali, "Microdetermination of Toluenediisocyanates in Atmosphere", Analytical Chemistry, Apr. 1957, pp. 552-558.

R. F. Walker et al., "Spectrophotometric Determination of Aliphatic Isocyanates in the Occupational Atmosphere", Analyst, Oct. 1979,, pp. 928-936.

Khama Rani Ghosh et al., "Direct detection of ultralow trace amounts of isocyanates in air using a fluorescent conjugated polymer", Chemical Communication, 2014, pp. 716-718.

Zhenzhong Gao et al., "A novel single-fluorophore-based ratiometric fluorescent probe for direct detection of isocyanates in air", Chemical Communication, 2017, pp. 6231-6234.

P. Saravana Kumar et al., "An easy to make chemoreceptor for the selective ratiometric fluorescent detection of cyanide in aqueous solution and in food materials", New Journal of Chemistry, 2019, pp. 675-680.

"International Search Report (Form PCT/ISA/210) of PCT/CN2019/113788," dated Mar. 27, 2020, with English translation thereof, pp. 1-2.

Enol form        Keto form

FLUORESCENT COMPOUND FOR DETECTION OF ISOCYANATE SUBSTANCES, PREPARATION METHOD AND USE THEREOF AS TEST-PAPER-TYPE DETECTION PROBE

CROSS-REFERENCE TO RELATED APPLICATION

This application is a 371 of international application of PCT application serial no. PCT/CN2019/113788, filed on Oct. 28, 2019, which claims the priority benefit of China application no. 201910581460.0, filed on Jun. 29, 2019. The entirety of each of the above mentioned patent applications is hereby incorporated by reference herein and made a part of this specification.

TECHNICAL FIELD

The present invention relates to the technical field of photochemistry detection and analysis, and specifically relates to a fluorescent compound for the detection of isocyanate substances, a preparation method therefor and use thereof as a test-paper-type detection probe.

BACKGROUND

Isocyanate mainly includes monoisocyanate, diisocyanate, polyisocyanate and other multiple compounds with a —NCO functional group. Due to the relatively high reactivity of its functional group, isocyanate, as a raw material, is widely applied in polyurethane (PU) industry, and used to produce various kinds of polyurethane articles. Moreover, isocyanate is a necessary component of insecticides, bactericides, herbicides, and the like; and also widely applied in industrial chemistry, drug preparation, agricultural sterilization and other fields. PU products (e.g., polyurethane adhesive) will release residual free isocyanate or isocyanate substances produced by degradation during the application process and use procedure. Isocyanate raw materials also may leak to environmental atmosphere in plants for producing PU products. Human may suffer thirst, cough, throat pain, even asthma and other symptoms if exposed to the air containing such kinds of substances for a short period of time; and if for a long time, the body may suffer severe harms of liver and lung function decline. Therefore, it is significant to develop a fluorescent compound capable of detecting the content of isocyanate in water and air efficiently and conveniently in terms of industrial safety, environment and human health.

Up to now, there are many methods for the analysis and detection of isocyanate, mainly including liquid chromatography, gas chromatographic method, absorption spectroscopy, fluorescent spectrometry, and the like. High performance liquid chromatography (HPLC) is a common international mainstream method for the detection of isocyanate substances at present; and the main principle is to make isocyanate substances react with a derivatization reagent to generate a stable derivative for measurement; and the common detector is an ultraviolet detector and a differential refractive index. For example, the literature (Analyst, 1991, 116, 21-25) has reported that different kinds of amine substances as a derivatization reagent, are subjected to derivation reaction with isocyanate, and then the derivatized products are detected by HPLC, thus achieving the detection to phenyl isocyanate substances. U.S. Pat. No. 6,656,737 has disclosed that 9-anthracenemethyl-1-piperazinecarboxylate is used as a derivatization reagent of isocyanate; and HPLC is used to detect the total amount of isocyanate monomers and isocyanate substances. The literature (Journal of Chromatography, 1988, 435, 469-481) has reported that HPLC is used to analyze substances containing 2,4-toluene diisocyanate, 2,6-toluene diisocyanate and related aminoisocyanates; and alkaline ethyl alcohol is mainly used as a derivatization reagent to detect the derivatization of isocyanate functional groups. A research paper published on Analytical Chemistry, 1981, 53, 1122-1125 has reported that N-methyl-1-naphthylmethylamine is used as a derivatization reagent to derivatize multiple isocyanate substances, thus detecting the derivatives thereof by liquid chromatography. However, the above method has a complex test procedure and high requirements, and long test period, thus being difficult to achieve portable, rapid and visual detection. Moreover, the method requires richer experience to choose proper derivatization reagents and proper detectors according to the properties of the substance detected. Gas chromatographic method is also a method for analyzing and measuring isocyanate compounds; and the main operating steps include the selection of the type of carrier gases, control of flow rate, preparation of a standard test solution, preparation of a buffer solution, preparation of a sample and chromatographic column, and the like. For example, the literature (Journal of Chromatography A, 1981, 208, 313-321) has reported that isocyanate is hydrolyzed into amine in diluted hydrochloric acid; and then derivatized by heptafluorobutyric anhydride; and gas chromatograph is used to detect isocyanate volatile matters existing in industrial waste gas. Moreover, in capillary gas chromatography of gas chromatography, it is unnecessary to fill in a packing; and the column efficiency is high. The literature (Analytical Chemistry, 1994, 66, 1664-1666) has reported that capillary gas chromatography is used to measure the content of 1,6-hexamethylene diisocyanate (HDI) in coatings. The literature (Journal of Chromatography A, 1985, 346, 191-204) has reported that capillary gas chromatography is used to detect isocyanate substances which may be possibly produced in the thermal degradation process of polyurethane polymers. However, the substance to be tested must be gasified when detected by a gas chromatographic method. Moreover, gasification temperature and other experiment conditions must be strictly controlled, and thus the gas chromatographic method has the disadvantages of complex analysis and test procedure, high demand for a sample, high restriction, higher operating experience to the equipment required, high cost of equipment, long test period, thus it is difficult to achieve portable and rapid application in detection.

Moreover, absorption spectroscopy is a measurement method based on the correlation between sample concentration and absorbance, and is also used to measure the content of isocyanate. For example, the literature (Analytical Chemistry, 1957, 29, 552-558) has reported that naphthylethylenediamine dihydrochloride is used as a derivatization reagent of toluene diisocyanate; and an absorption spectrophotometer is used to detect the toluene diisocyanate volatile matters residual in air. An article published on (Analyst, 1979, 104, 928-936) has reported an absorption spectroscopy for measuring the content of aliphatic isocyanate and oligomers thereof in air; isocyanate substances were dissolved in corresponding amine for derivatization reaction, and then absorbance of a derivative was measured, thus obtaining the content of isocyanate. But absorption spectroscopy has low detection accuracy and sensitivity; further, incomplete hydrolysis of isocyanate results in large difference between the measured result and the actual value, higher amount of the sample required, longer developing process, and other problems. Fluorescent spectrometry is an easy-to-use detection method having good selectivity and high sensitivity, and also can be used for the detection and analysis of isocyanate substances. The journal article (*Chemical Communication,* 2014, 50, 716-718) has reported a polymer for detecting isocyanate; when there is volatile isocyanate in atmospheric air, the fluorescence of the polymer will turn-off, thus detecting the isocyanate. However, the polymer has a complex structure and is difficult to be prepared; meanwhile, the probe may be further influenced by many factors, resulting in fluorescence turning off, thereby causing a false positive result to affect the detection performance. The literature (*Chemical Communication,* 2017, 53, 6231-6234) has reported a ratiometric fluorescent small-molecule based on anthracene imide; after isocyanate reacts with hydroxyl on an aromatic ring of the fluorescent molecule, the push-pull electronic effect in the molecule changes to cause the change of fluorescence color, thus achieving the detection of isocyanate. But synthesis of the molecule is complex, and requires a large amount of dangerous and irritating chemical reagents, e.g., oxalyl chloride, during the preparation, which is bad for environmental protection; meanwhile, the preparation procedure is rather long which results in low final yield, and is not beneficial to mass production. The fluorescent probe compounds for the detection of isocyanate substances reported currently are basically traditional aggregation-caused-quenching fluorescent compounds and thus, do not have aggregation-induced fluorescence enhancement effect. Therefore, these fluorescent probe compounds always cause fluorescence turning-off due to aggregation when used as solid detectors (e.g., a test paper), so that the fluorescent quantum yield of test paper and other solid detectors is low with weaker luminescence, thus affecting the detection performance.

Even though researchers have achieved certain progress in the studies on fluorescent compounds for the detection of isocyanate currently, but there is few detection system having the following characteristics at the same time: (1) rapid response rate, sensitivity and strong specific recognition capability to isocyanate substances; (2) simple preparation process, high yield, rich and easy-to-get raw material resources for the preparation; (3) the fluorescent probe compound has aggregation-induced emission feature; therefore, the test-paper-type solid probe has high fluorescence quantum yield and high emission intensity; (4) the system can be used for the detection of liquid isocyanate, and also can be constructed as a test-paper-type solid probe for the detection of gaseous isocyanate; (5) the change of color and fluorescence before and after response can be distinguishable directly by naked eyes. Therefore, the development of a fluorescent detection probe having the above characteristics can achieve more convenient, sensitive, and visual detection and analysis for isocyanate.

SUMMARY

Technical Problem

To overcome the above shortcomings in the prior art, the objective of the present invention is to provide a fluorescent compound for the detection of isocyanate substances, a preparation method and use thereof as a test-paper-type detection probe.

The primary objective of the present invention is to develop a fluorescent probe having aggregation-induced emission (AIE) effect and sensitive detection to isocyanate.

Another objective of the present invention is to provide a simple, rapid and high-yield method for preparing the above fluorescent compound.

A further objective of the present invention is to provide use of the above fluorescent compound in the detection of isocyanate, and to provide a test-paper-type probe for portable, rapid, visualizable and in-situ response to isocyanate with fluorescence alteration.

Solution to Problem

Technical Solution

The objectives of the present invention are at least achieved by one of the following technical solutions:

The present invention provides a fluorescent compound (a fluorescent probe) for the detection of isocyanate substances; the fluorescent compound has the chemical name of 2,4-di(((4'-(diphenylamino)-[1,1'-biphenyl]-4-yl)imino) methyl)phenol, a molecular formula of $C_{56}H_{42}N_4O$, a molecular weight of 786.33, is abbreviated to BTPAP and has the structural formula below

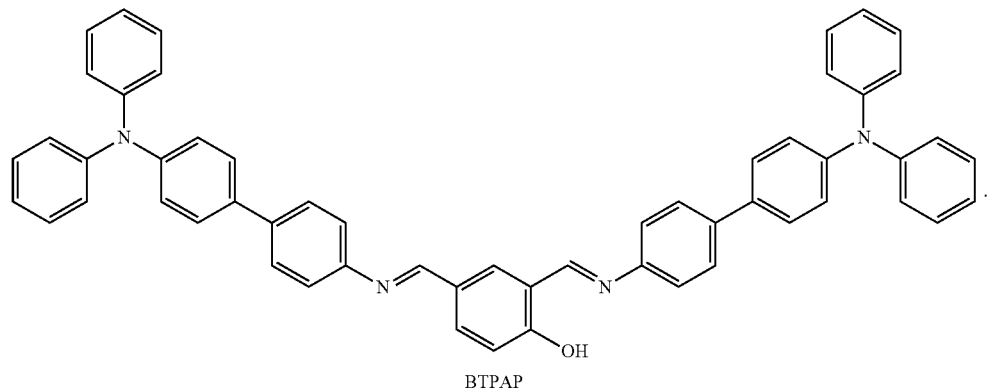 [SMILES: Oc1ccc(/C=N/c2ccc(-c3ccc(N(c4ccccc4)c4ccccc4)cc3)cc2)cc1/C=N/c1ccc(-c2ccc(N(c3ccccc3)c3ccccc3)cc2)cc1]

BTPAP

The present invention provides a method for preparing a fluorescent compound for the detection of isocyanate substances; and the preparation has the following reaction formula:

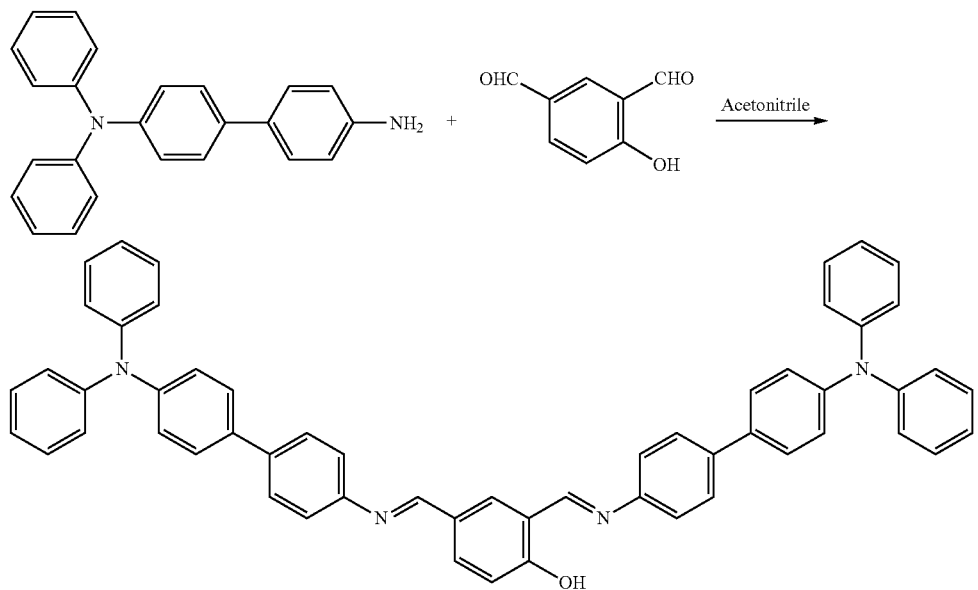

The present invention provides a method for preparing a fluorescent compound for the detection of isocyanate substances, including the following steps of:

(1) dissolving N,N-diphenyl-[1,1'-biphenyl]-4,4'-diamine in acetonitrile with homogeneous ultrasonic agitation to obtain solution 1;

(2) dissolving 4-hydroxyisophthalaldehyde in acetonitrile with homogeneous ultrasonic agitation to obtain solution 2;

(3) dissolving potassium carbonate in deionized water with homogeneous ultrasonic agitation to obtain an aqueous solution of potassium carbonate; and (4) mixing solution 1 with solution 2 evenly to obtain solution 3, and then adding the aqueous solution of potassium carbonate in step (3) into solution 3, and then placing solution 3 under vacuum, charging solution 3 with nitrogen, heating solution 3, then cooling solution 3 to room temperature to obtain a product after the cooling step, then separating and purifying the product to obtain an orange-yellow powder; namely, the fluorescent compound for the detection of isocyanate substances.

Further, a molar ratio of the N,N-diphenyl-[1,1'-biphenyl]-4,4'-diamine to the 4-hydroxyisophthalaldehyde is (2-5):1.

Further, a molar ratio of the N,N-diphenyl[1,1'-biphenyl]-4,4'-diamine to the potassium carbonate is 1:(1-10).

Further, in solution 1 of step (1), N,N-diphenyl-[1,1'-biphenyl]-4,4'-diamine has a concentration of 0.01 M-0.1 M; and in solution 2 of in step (2), 4-hydroxyisophthalaldehyde has a concentration of 0.01 M-0.1 M.

Further, the aqueous solution of potassium carbonate in step (3) has a concentration of 1-6 mol/L.

Further, the heating in step (4) has a temperature of 25-120° C.; and the heating lasts for 3 hours to 24 hours.

Further, the separating and purifying solution 3 in step (4) include the following steps of: extracting solution 3 with dichloromethane and deionized water; collecting an organic phase of solution 3 and drying the organic phase of solution 3 by anhydrous sodium sulfate; distilling the organic phase of solution 3 under reduced pressure to remove solvents, and subjecting the organic phase of solution 3 to column chromatography on silica gel for further separation and purification.

The present invention provides use of the fluorescent compound for the detection of isocyanate substances as a test-paper-type detection probe in analysis and detection of isocyanate substances.

The above test-paper-type probe is used to the method for the detection of isocyanate, including the following steps of:

dissolving 2,4-di(((4'-(diphenylamino)-[1,1'-biphenyl]-4-yl)imino)methyl)phenol (abbreviated to BTPAP) in dichloromethane, preparing and obtaining a stock solution of the fluorescent compound; dropwise adding the stock solution on a Whatman filter paper, and after complete wetting and with natural air drying to obtain a test-paper-type probe; exposing the probe with the analyte (polluted air or water source); where if the probe shows bright blue fluorescence (at 425 nm), it indicates that the analyte contains isocyanate substances.

The fluorescent compound for the detection of isocyanate substances provided by the present invention is 2,4-di(((4'-(diphenylamino)-[1,1'-biphenyl]-4-yl)imino)methyl)phenol (abbreviated to BTPAP), and has a molecular formula of $C_{56}H_{42}N_4O$, a molecular weight of 786.33. The fluorescent compound BTPAP is a solid orange-yellow powder, easy to be dissolved in dichloromethane (DCM), tetrahydrofuran (THF), dimethyl sulfoxide (DMSO) and other solvents. The compound has good photo-stability, good physical stability and a stable chemical structure, and is non-toxic and difficult to sublimate, and suitable for long-term storage and use. Moreover, under the condition of illumination, the fluorescent probe BTPAP has a rapid photoisomerization process due to excited state intramolecular proton transfer (ESIPT); and the molecular structure makes a reversible transformation (the schematic diagram of transformation of a specific structure is shown in FIG. 1) between Enol form and Keto form; therefore, BTPAP merely shows weakly dark orange fluorescence (at 580 nm).

When the test-paper-type probe containing BTPAP is immersed into a solution containing isocyanate or exposed to the air containing isocyanate, BTPAP and isocyanate are subjected to chemical reaction; then the phenolic hydroxyl in the molecular structure is transformed into carbamate to generate new substances (BTPAP-iso); and the mechanism of action is shown in FIG. 2 below. New substance is free from the ESIPT effect and thus shows strongly bright blue fluorescence at 425 nm. Due to the feature of aggregation-induced emission, the fluorophore BTPAP-iso in the test-paper probe has high fluorescence quantum yield and strong luminescence, capable of achieving sensitive detection. The fluorescent probe compound of the present invention can be applied to industrial production or environmental monitoring process for the selective detection and visualized analysis of isocyanate liquids and gases.

The present invention provides a fluorescent probe used for the detection of isocyanate substances; the probe has significantly-changed and enhanced fluorescence in the presence of isocyanate substances, thus achieving the portable, sensitive, and in-situ visual detection for isocyanate in a solution or on a test paper.

Effect of Invention

Beneficial Effect

Compared with the prior art, the present invention has the following advantages and beneficial effects:

(1) the fluorescent compound BTPAP for the detection of isocyanate substances provided by the present invention reacts with isocyanate substances, and then an electron-donating arylhydroxy (the recognition group) thereon transforms into electron-attracting carbamate to prevent the ESIPT effect in the original structure, thus rapidly producing strong fluorescence; and with the increase of isocyanate substance concentration, the fluorescence enhances, thereby achieving the sensitive detection to isocyanate;

(2) the fluorescent compound BTPAP for the detection of isocyanate substances provided by the present invention has a weak fluorescence emission peak at 580 nm; and after reacting with isocyanate, the newly produced substance (BTPAP-iso) has strong fluorescence emission; and the fluorescence peak shifts to around 425 nm; the wavelength range of the fluorescence emission before and after reaction is not overlapped; and thus the color distinguishability is relatively high and the influence of background fluorescence is reduced; therefore, the present invention can be used for the visual detection by naked eyes;

(3) the fluorescent compound BTPAP for the detection of isocyanate substances provided by the present invention has two triphenylamine groups, and can endow the probe with aggregation-induced emission feature, thus ensuring high fluorescence quantum yield and intense luminescence after reacting with isocyanate in a solid probe (e.g., a test-paper-type probe), which is beneficial for improving the detection effect; moreover, the prepared fluorescence detection test paper has simple process. A method of the fluorescent compound (as a test-paper-type probe) for the detection of isocyanate substances provided by the present invention used in the analysis and detection of isocyanate substances is a method for the detection of isocyanate gases having good detection selectivity and high sensitivity, which is capable of achieving convenient, rapid and in-situ sensitive detection and is easy to use;

(4) the fluorescent compound BTPAP for the detection of isocyanate substances provided by the present invention is prepared by means of a one-step method. The fluorescent compound has simple and convenient preparation with high yield, and is suitable for large-scale industrial production. Moreover, the fluorescent compound has the advantages of simple chemical process, ease in design, no complex post-treatment process, rich and accessible raw materials, and moderate price.

BRIEF DESCRIPTION OF THE DRAWINGS

Description of the Drawings

Figure 1:
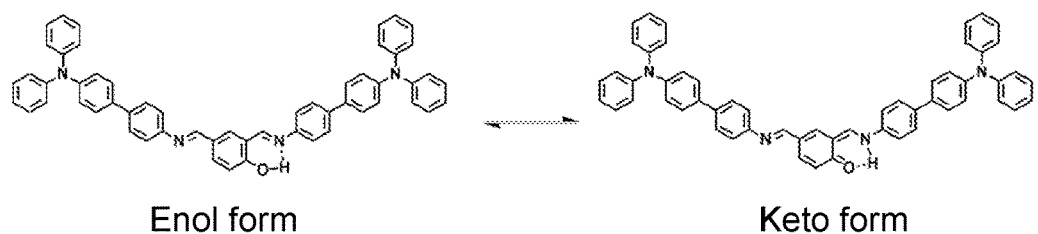
Figure 2:
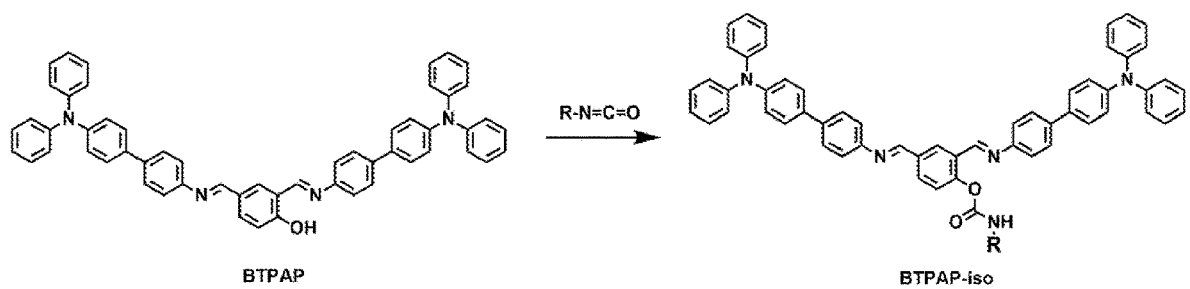
Figure 3:
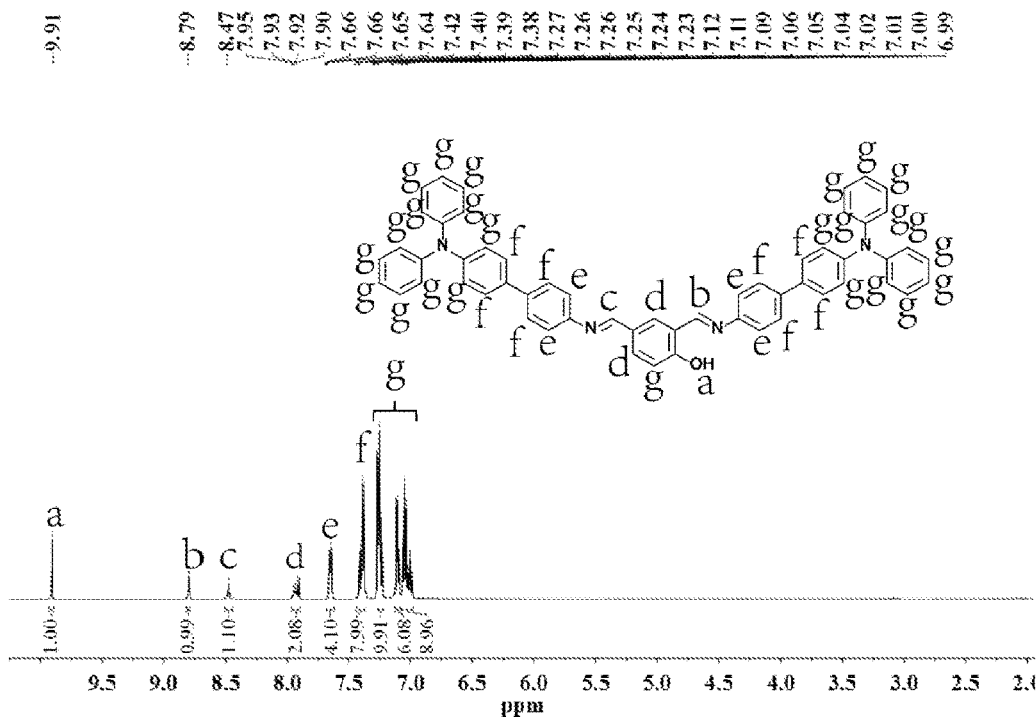

FIG. 1 is a schematic diagram showing that a fluorescent compound for the detection of isocyanate substances provided by the present invention transforms between Enol form and Keto form structures;

FIG. 2 is a schematic diagram showing the response mechanism that the fluorescent compound for the detection of isocyanate substances provided by the present invention makes a response to isocyanate;

FIG. 3 is a Hydrogen Nuclear Magnetic Resonance ($^1$H NMR) of 2,4-di(((4'-(diphenylamino)-[1,1'-biphenyl]-4-yl)imino)methyl)phenol prepared in Example 1.

Figure 4:
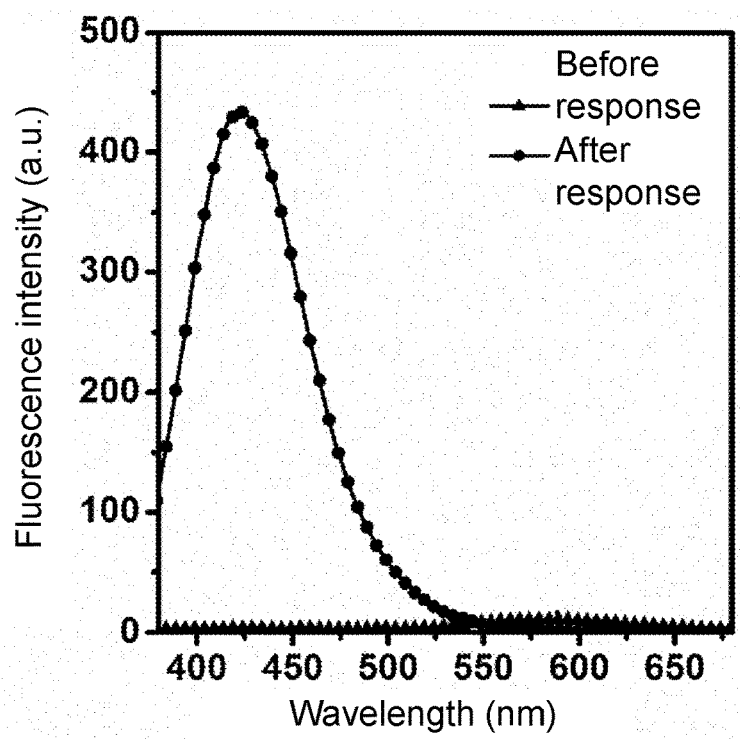

FIG. 4 is fluorescence spectra of the fluorescent compound for the detection of isocyanate substances provided by the present invention as a fluorescent probe before and after making a response to isocyanate.

Figure 5:
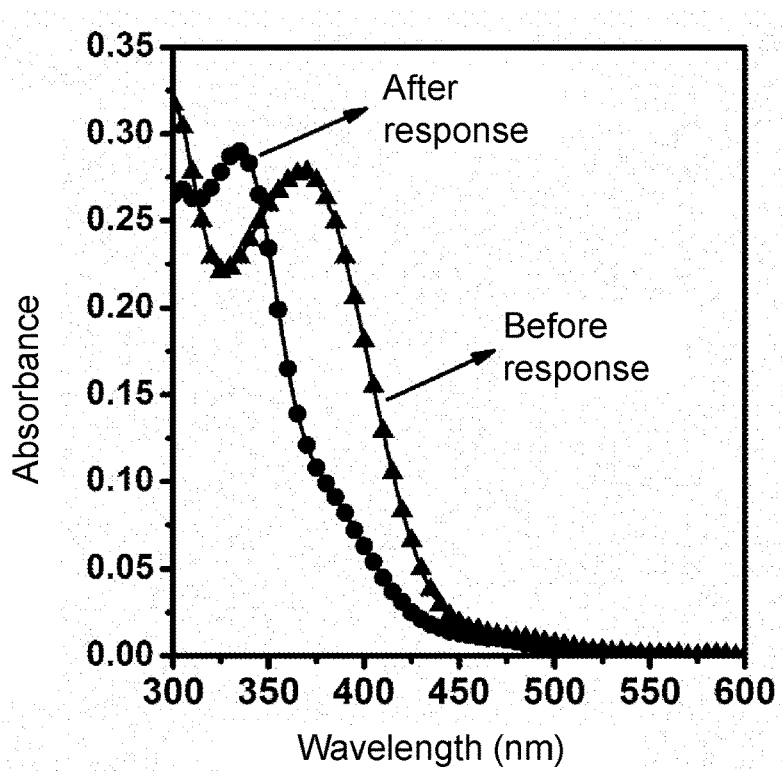

FIG. 5 is absorption spectra of the fluorescent compound for the detection of isocyanate substances provided by the present invention as a fluorescent probe before and after making a response to isocyanate.

Figure 6:
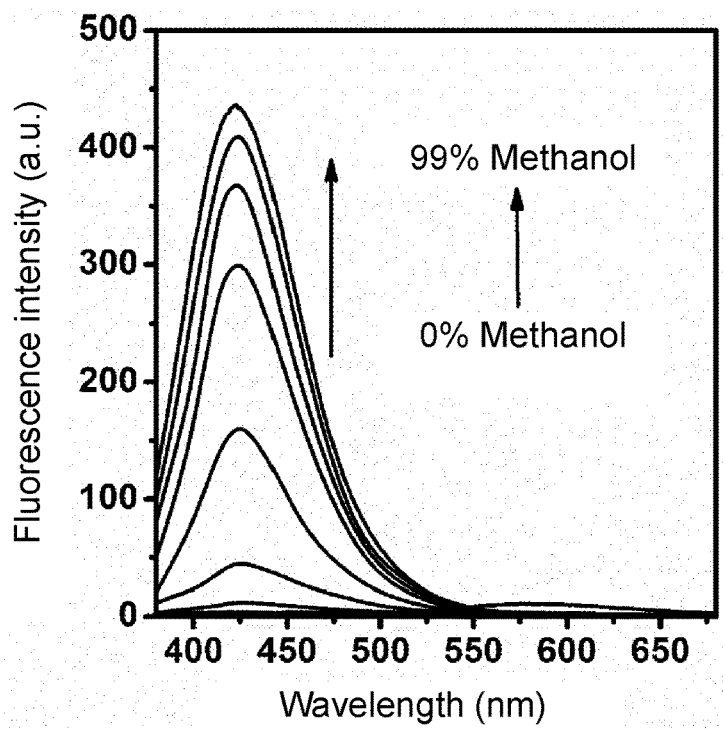

FIG. 6 is fluorescence spectra of a reaction product BTPAP-iso in Example 4 in a mixed solution of dichloromethane/methanol in varying proportions.

Figure 7:
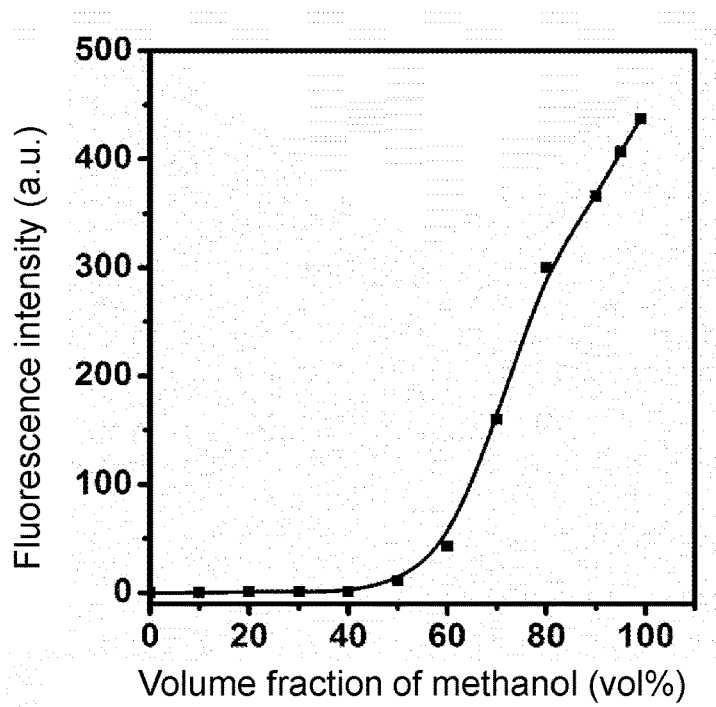

FIG. 7 is a diagram showing fluorescence intensity changes of BTPAP-iso in Example 4 at 425 nm in a mixed solution of dichloromethane/methanol in varying proportions.

Figure 8:
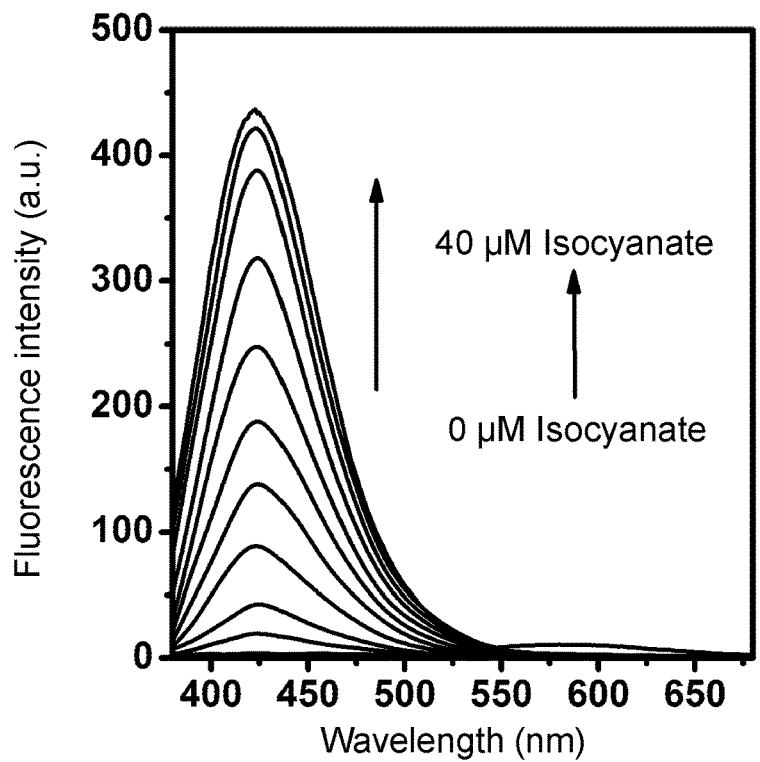

FIG. 8 is fluorescence spectra of the fluorescent compound BTPAP for the detection of isocyanate substances prepared in Example 4 in response to different concentrations of isocyanate.

Figure 9:
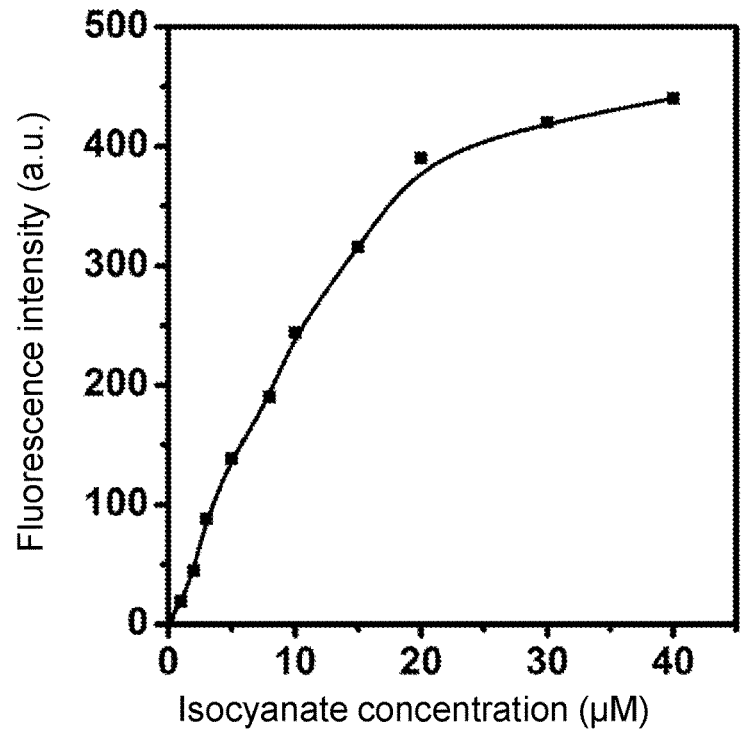

FIG. 9 is a diagram showing fluorescence intensity of the fluorescent compound BTPAP for the detection of isocyanate substances prepared in Example 4 in response to different concentrations of isocyanate.

DETAILED DESCRIPTION

Embodiments of the Invention

Detailed embodiments of the present invention will be further described in detail in combination with the accompanying drawings and examples, but embodiments of the present invention are not limited thereto. It needs to be pointed that any process not specified particularly in detail below should be achieved or understood by reference to the prior art by a person skilled in the art. Any reagent or instrument not marked with a manufacturer should be regarded as a conventional product available in the market.

The chemical equation for preparing the fluorescent compound for the detection of isocyanate substances in examples is as follows:

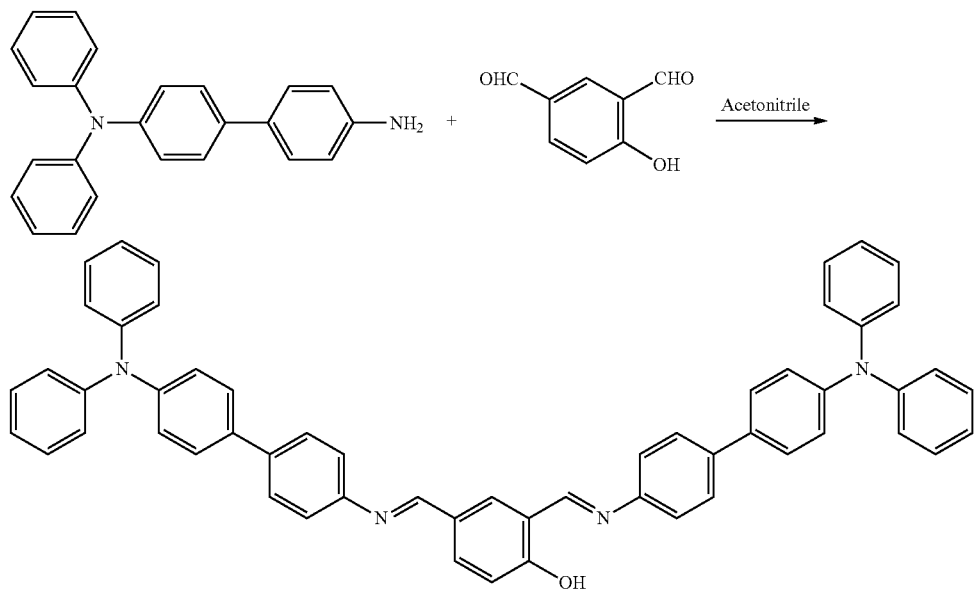

Example 1

A method for preparing a fluorescent compound for the detection of isocyanate substances, including the following steps of:

(1) 672 mg N,N-diphenyl-[1,1'-biphenyl]-4,4'-diamine was dissolved in 20 mL acetonitrile with homogenous ultrasonic agitation to obtain a solution 1;

(2) 150 mg 4-hydroxyisophthalaldehyde was dissolved in 10 mL acetonitrile with homogenous ultrasonic agitation to obtain a solution 2;

(3) meanwhile, 138 mg potassium carbonate was dissolved to deionized water with homogenous ultrasonic agitation evenly to obtain a 1 mol/L aqueous solution of potassium carbonate; and (4) the solution 1 in step (1) and the solution 2 in step (2) were mixed evenly, and then dropwise added into 1 mol/L aqueous solution of potassium carbonate prepared in step (3), vacuumized and nitrogen was charged, a heating reaction was carried out for 3 hours, where the reaction temperature was controlled at 25° C.; then the reaction was stopped, after cooling to room temperature, then the obtained product was separated and purified to obtain 565.9 mg orange-yellow powder, 2,4-di(((4'-(diphenylamino)-[1, 1'-biphenyl]-4-yl)imino)methyl)phenol, namely, the fluorescent compound (BTPAP) for the detection of isocyanate substances with a yield of 72%;

The product was characterized by H-NMR below: $^1$H NMR (600 MHz, DMSO-d6) δ 9.91 (s, 1H), 8.79 (s, 1H), 8.47 (s, 1H), 7.93 (dd, J=17.1, 9.0 Hz, 2H), 7.65 (dd, J=8.2, 3.2 Hz, 4H), 7.40 (dd, J=15.6, 8.3 Hz, 8H), 7.27-7.23 (m, 10H), 7.13-7.08 (m, 6H), 7.07-6.98 (m, 9H). Particularly, "a" having a chemical shift at 9.91 ppm belonged to a hydroxyl proton characteristic peak; "b" and "c" at 8.79 ppm and 8.47 ppm respectively belonged to proton characteristic peaks on a Schiff base structure; proton peaks at 7.93 ppm and 7.65 ppm mainly belonged to characteristic peaks of a benzene ring structure connected with triphenylamine; "g" at 7.3-6.9 ppm mainly belonged to a proton characteristic peak on three aromatic rings of triphenylamine. By the analysis of NMR, it can be determined that the synthesized product was a target product. The HNMR thereof was shown in FIG. 3.

Example 2

A method for preparing a fluorescent compound for the detection of isocyanate substances, including the following steps of:

(1) 1008 mg N,N-diphenyl-[1,1'-biphenyl]-4,4'-diamine was dissolved in 50 mL acetonitrile with homogenous ultrasonic agitation evenly to obtain a solution 1;

(2) 150 mg 4-hydroxyisophthalaldehyde was dissolved in 50 mL acetonitrile with homogenous ultrasonic agitation evenly to obtain a solution 2;

(3) 690 mg potassium carbonate was dissolved in deionized water with homogenous ultrasonic agitation evenly to obtain a 3 mol/L aqueous solution of potassium carbonate; and (4) the solution 1 in step (1) and the solution 2 in step (2) were mixed evenly, and then dropwise added into 3 mol/L aqueous solution of potassium carbonate prepared in step (3), vacuumized and nitrogen was charged, a heating reaction was carried out for 12 hours, where the reaction temperature was controlled at 70° C.; then the reaction was stopped, after cooling to room temperature, then the obtained product was separated and purified to obtain 644.5 mg orange-yellow powder, 2,4-di(((4'-(diphenylamino)-[1, 1'-biphenyl]-4-yl)imino)methyl)phenol, namely, the fluorescent compound (BTPAP) for the detection of isocyanate substances with a yield of 82%.

The characterization of the fluorescent probe compound BTPAP obtained in this example was the same as the characterization result in Example 1, referring to FIG. 3.

Example 3

A method for preparing a fluorescent compound for the detection of isocyanate substances, including the following steps of:

(1) 1680 mg N,N-diphenyl-[1,1'-biphenyl]-4'-diamine was dissolved in 500 mL acetonitrile with homogenous ultrasonic agitation evenly to obtain a solution 1;

(2) 150 mg 4-hydroxyisophthalaldehyde was dissolved in 100 mL acetonitrile for with homogenous ultrasonic agitation evenly to obtain a solution 2;

(3) 1380 mg potassium carbonate was dissolved in deionized water with homogenous ultrasonic agitation evenly to obtain a 6 mol/L aqueous solution of potassium carbonate; and (4) the solution 1 in step (1) and the solution 2 in step (2) were mixed evenly, and then dropwise added into 6 mol/L aqueous solution of potassium carbonate prepared in step (3), vacuumized and nitrogen was charged, a heating reaction was carried out for 24 hours, where the reaction temperature was controlled at 120° C.; then the reaction was stopped, after cooling to room temperature, then the obtained product was separated and purified to obtain 707.4 mg orange-yellow powder, 2,4-di(((4'-(diphenylamino)-[1,1'-biphenyl]-4-yl)imino)methyl)phenol, namely, the fluorescent compound (BTPAP) for the detection of isocyanate substances with a yield of 90%.

The characterization of the fluorescent probe compound (BTPAP) obtained in this example was the same as the characterization result in Example 1, referring to FIG. 3.

Example 4

Test on Spectroscopic Performance.

(1) Measurement of Fluorescence Spectra and Absorption Spectra of a Fluorescent Compound BTPAP Before and after Making a Response to Isocyanate:

1.6 mg fluorescent compound 2,4-di(((4'-(diphenylamino)-[1,1'-biphenyl]-4-yl)imino)methyl)phenol was dissolved to 2 mL DCM and prepared into a stock solution of the fluorescent compound having a concentration of 1 mM. During test, the fluorescent compound kept a concentration of 5 µM, and total volume of the test system was kept 3 mL (containing dichloromethane having a volume percent of 10%); isocyanate compounds included multiple kinds of compounds containing an isocyanate group; in this example, chloroethyl isocyanate was used as a model analyte; an isocyanate solution was dropwise added to a probe BTPAP solution at 25° C., shaken for 5 minutes to test the response performance of BTPAP to isocyanate; and test results were shown in FIGS. 4 and 5. It can be seen from FIGS. 4 and 5 that after making a response to isocyanate, emission wavelength and absorption spectrum showed a certain degree of blue shift; this was because the ESIPT effect disappeared after isocyanate reacted with aromatic hydroxy, resulting in the failure of the transformation between Enol form and Keto form; and meanwhile, the electronic effect also changed, resulting in the blue shift and enhancement of fluorescence emission.

(2) Test on the Aggregation-Induced Emission Feature of BTPAP-Iso:

When the fluorescent compound BTPAP was subjected to a chemical reaction with isocyanate, the phenolic hydroxyl group in molecules was transformed to carbamate, thus generating a new substance (BTPAP-iso). Test on the aggregation-induced emission feature of BTPAP-iso was performed below.

A mixed solution of dichloromethane and methanol in different volume fractions was prepared, of which the volume percent of methanol was respectively 0%, 10%, 20%, 30%, 40%, 50%, 60%, 70%, 80%, 90%, 95%, and 99%; during test, BTPAP-iso had a concentration of 5 µM; the test temperature was room temperature; 360 nm was adopted as excitation wavelength; and the measured spectra were shown in FIG. 6; and the fluorescence intensity at 425 nm with the change of volume fraction of methanol was shown in FIG. 7. It can be seen from FIG. 7 that in a test solution system having a relatively small volume fraction of methanol (<50%), the solution had weak fluorescence; when the volume fraction of methanol increased gradually, fluorescence intensity enhanced gradually, especially when the volume fraction of methanol increased to 99%, fluorescence intensity increased to the maximum. This is because the probe molecule had better solubility in dichloromethane, and its molecule can rotate and vibrate in the solution freely; and electron can dissipate the excited energy via intramolecular movements when the excited-state electrons return to the ground state, making fluorescence weak; while with the increase of the volume fraction of a poor solvent, such as methanol, it makes the space for intramolecular free rotation and vibration in the test solution system smaller and smaller, and even makes molecules agglomerated together due to the decrease of solubility, thus opening the radiative pathway that the excited-state electrons transit to the ground state, thus capable of releasing fluorescence, which reflects the characteristic of aggregation-induced emission phenomenon fully. Moreover, it can be further seen from FIG. 7 that a quantification curve of the fluorescence intensity at 425 nm versus the increase of the volume fraction of methanol also indicates the presence of the above phenomenon.

(3) Response Test of a BTPAP Fluorescent Probe to Different Concentrations of Isocyanate:

Different concentrations of isocyanate test sample solutions (concentrations were respectively 0 µM, 1 µM 2 µM, 3 µM, 5 µM, 8 µM, 10 µM, 15 µM, 20 µM, 30 µM, and 40 µM) were prepared. During test procedure, the probe concentration was kept 5 µM, and the volume fraction of DCM and methanol was 1/99; the test temperature was room temperature; the response time was 5 min; 360 nm served as excitation wavelength to measure the fluorescence spectra (fluorescence intensity at 425 nm) of the fluorescent probe in response to different concentrations of isocyanate; and the test results were shown in FIG. 8. Moreover, the fluorescence intensity curves to different concentrations of isocyanate were shown in FIG. 9. It can be seen from FIG. 8 that the fluorescent compound prepared by the present invention had a good response effect to different concentrations of isocyanate; and with the increase of the isocyanate concentration, the fluorescence intensity also enhanced gradually. It can be seen from FIG. 9 that the fluorescence enhancement amplitude slowed down when the isocyanate concentration was up to 20 µM, indicating that the reaction system became saturated. Thus, the probe prepared by the present invention is suitable for detecting different concentrations of isocyanate, and has a wider scope of application concentration.

Example 5

Response Test of a Test-Paper-Type Fluorescent Probe Containing BTPAP to Different Concentrations of Isocyanate:

1 mM fluorescent probe BTPAP stock solution was prepared, and evenly dropped onto a Whatman filter paper, then air dried naturally at room temperature, and prepared into a test-paper-type probe (appeared apparent yellow), afterwards, a test paper was suspended in an isocyanate atmosphere having a concentration of 5 µM, standing for 5 minutes, the change of apparent color can be seen under visible light; and in the presence of isocyanate substances, the test paper changed to white from apparent yellow, and the color change can be visible by naked eyes. Moreover, the test paper was respectively placed in different concentrations (0 μM-5 μM) of isocyanate atmosphere, after standing for 5 minutes, a variation diagram of fluorescence under the irradiation of a 15 W 365 nm portable UV lamp can be observed directly; it can be seen that the fluorescence intensity of the probe enhanced and fluorescence color gradually changed to bright blue from dark orange with the increase of isocyanate concentration under the excitation at 365 nm. On the other hand, the probe molecule itself has better aggregation-induced emission effect, and has very strong fluorescence intensity due to high fluorescence quantum yield in solid aggregation state. The above results indicate that the test-paper-type probe prepared by the probe molecule can make a response to isocyanate, and has visible changes observable by naked eyes. Moreover, the test-paper-type probe has simple preparation process, easy operation, and is easy to carry, store and use.

In the present invention, the fluorescent probe molecule 2,4-di(((4'-(diphenylamino)-[1,1'-biphenyl]-4-yl)imino) methyl)phenol (BTPAP) can be used to detect isocyanate; and the probe molecule (the fluorescent compound used for the detection of isocyanate substances) has AIE feature itself, and has changed and enhanced fluorescence with the increase of the isocyanate concentration in a test solution, larger range of fluorescence variation, and has high distinguishable degree of color. Furthermore, the present invention can be prepared into a test-paper-type probe, suitable for the detection of volatile isocyanate substances existing in air; and the color change of the test-paper-type probe can be visible by naked eyes under visible light in the presence of isocyanate; and under a 365 nm UV lamp, the fluorescence intensity of the test-paper-type probe makes blue shift and enhancement with the increase of isocyanate gas concentration. The above results indicate that the fluorescent probe prepared by the present invention can be used for the detection of isocyanate substances in a solution and of gaseous isocyanate substances, and specifically can be used to monitor isocyanate, such a hazardous substance in atmospheric air, water resources, working space of a factory and industrial wastewater.

The above examples are only preferred embodiments of the present invention, and only used for explaining the present invention, but not limiting the present invention. Moreover, any alteration, replacement, modification and the like made by a person skilled in the art within the spirit of the present invention shall fall within the protection scope of the present invention.

What is claimed is:

1. A fluorescent compound for detection of isocyanate substances, wherein the fluorescent compound has the chemical name of 2,4-di(((4'-(diphenylamino)-[1,1'-biphenyl]-4-yl)imino)methyl)phenol, a molecular formula of $C_{56}H_{42}N_4O$, a molecular weight of 786.33, and has the structural formula of

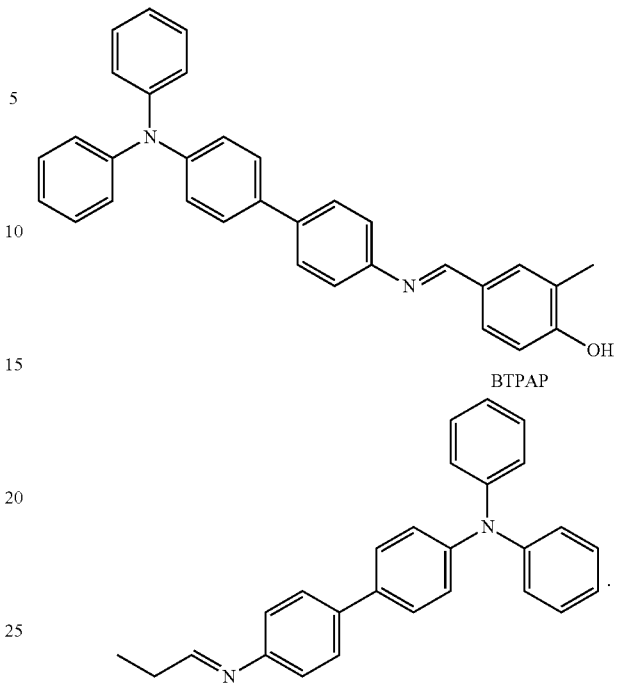

2. A method for preparing the fluorescent compound for the detection of isocyanate substances of claim 1, wherein the preparation comprising the following steps of:
   step (1) dissolving N,N-diphenyl-[1,1'-biphenyl]-4,4'-diamine in acetonitrile with homogeneous ultrasonic agitation to obtain solution 1;
   step (2) dissolving 4-hydroxyisophthalaldehyde in acetonitrile with homogeneous ultrasonic agitation to obtain solution 2;
   step (3) dissolving potassium carbonate in water with homogeneous ultrasonic agitation to obtain an aqueous solution of potassium carbonate; and
   step (4) mixing solution 1 with solution 2 to obtain solution 3, and then adding the aqueous solution of potassium carbonate in step (3) into solution 3, and then placing solution 3 under vacuum, charging solution 3 with nitrogen, heating solution 3, cooling solution 3 to room temperature to obtain a product after the cooling step, then separating and purifying the product to obtain the fluorescent compound for the detection of isocyanate substances.

3. The method for preparing the fluorescent compound for the detection of isocyanate substances according to claim 2, wherein a molar ratio of the N,N-diphenyl[1,1'-biphenyl]-4,4'-diamine to the 4-hydroxyisophthalaldehyde is (2-5).

4. The method for preparing the fluorescent compound for the detection of isocyanate substances according to claim 2, wherein a molar ratio of the N,N-diphenyl-[1,1'-biphenyl]-4,4'-diamine to the potassium carbonate is 1:(1-10).

5. The method for preparing the fluorescent compound for the detection of isocyanate substances according to claim 2, wherein in solution 1 of step (1), N,N-diphenyl-[1,1'-biphenyl]-4,4'-diamine has a concentration of 0.01 M-0.1 M; and in solution 2 of step (2), 4-hydroxyisophthalaldehyde has a concentration of 0.01 M-0.1 M.

6. The method for preparing the fluorescent compound for the detection of isocyanate substances according to claim 2, wherein the aqueous solution of potassium carbonate in step (3) has a concentration of 1-6 mol/L.

7. The method for preparing the fluorescent compound for the detection of isocyanate substances according to claim 2, wherein the heating in step (4) has a temperature of 25-120° C.; and the heating lasts for 3 hours to 24 hours.

8. The method for preparing the fluorescent compound for the detection of isocyanate substances according to claim 2, wherein the separating and purifying the product in step (4) comprises the following steps of: extracting solution 3 with dichloromethane and deionized water; collecting an organic phase of solution 3 and drying the organic phase of solution 3 by anhydrous sodium sulfate; distilling the organic phase of solution 3 under reduced pressure to remove solvents, and subjecting the organic phase of solution 3 to column chromatography on silica gel.

\* \* \* \* \*